(12) United States Patent
Alshemari

(10) Patent No.: US 8,961,510 B2
(45) Date of Patent: Feb. 24, 2015

(54) ENDOSCOPIC NASAL PALATOPLASTY

(76) Inventor: Hasan M. Alshemari, Saad Al-Abdulla (KW)

(*) Notice: Subject to any disclaimer, the term of this patent is extended or adjusted under 35 U.S.C. 154(b) by 303 days.

(21) Appl. No.: 13/587,251

(22) Filed: Aug. 16, 2012

(65) Prior Publication Data
US 2013/0053845 A1    Feb. 28, 2013

Related U.S. Application Data

(63) Continuation of application No. 13/219,580, filed on Aug. 26, 2011.

(51) Int. Cl.
*A61B 18/12* (2006.01)
*A61B 1/018* (2006.01)
*A61B 1/233* (2006.01)

(52) U.S. Cl.
CPC ............... *A61B 1/018* (2013.01); *A61B 1/233* (2013.01)
USPC ............. 606/46; 606/32; 606/41; 606/49

(58) Field of Classification Search
CPC ............ A61B 2018/00327; A61B 2018/00321
USPC ...................................................... 606/44, 46
See application file for complete search history.

(56) References Cited

U.S. PATENT DOCUMENTS

| | | | | |
|---|---|---|---|---|
| 4,887,593 A * | 12/1989 | Wiley et al. | ...................... | 606/45 |
| 5,429,131 A * | 7/1995 | Scheinman et al. | .......... | 600/374 |
| 5,505,728 A * | 4/1996 | Ellman et al. | .................... | 606/39 |
| 5,879,349 A * | 3/1999 | Edwards | ......................... | 606/45 |
| 6,053,172 A * | 4/2000 | Hovda et al. | .................... | 128/898 |
| 6,439,238 B1 * | 8/2002 | Brenzel et al. | ................ | 128/898 |
| 2009/0131923 A1 * | 5/2009 | Connors et al. | ................. | 606/10 |

OTHER PUBLICATIONS

Prior art cited in parent U.S. Appl. No. 13/219,580, filed Aug. 26, 2011, the priority of which is claimed herein.

* cited by examiner

*Primary Examiner* — Jaymi Della
(74) *Attorney, Agent, or Firm* — Richard C Litman

(57) ABSTRACT

The endoscopic nasal palatoplasty procedure provides a reduction in the posterior aspect of the soft palate and/or uvula, thereby increasing the area of the nasopharyngeal passage between the soft palate and/or uvula and the back of the nasopharynx. This increased nasopharyngeal area promotes nasal breathing, thereby reducing reliance upon oral breathing and corresponding sleep-disordered breathing syndrome and associated problems such as sleep apnea and snoring. The procedure is performed using a conventional surgical implement, such as a Coblator® or other electro cauterizing or laser cauterizing implement, to ablate and cauterize a series of lesions in the soft palate and/or uvula. The procedure is performed by inserting the surgical implement through one of the nasal passages to access the superior surface of the soft palate and/or uvula.

10 Claims, 4 Drawing Sheets

ENDOSCOPIC NASAL PALATOPLASTY

CROSS-REFERENCE TO RELATED APPLICATIONS

This is a continuation of my prior application Ser. No. 13/219,580, filed Aug. 26, 2011 now pending.

BACKGROUND OF THE INVENTION

1. Field of the Invention

The present invention relates generally to methods and surgical procedures for treating sleep-disordered breathing, and particularly to an endoscopic nasal palatoplasty procedure using an instrument inserted endonasally to perform procedures on the soft palate and/or uvula.

2. Description of the Related Art

Various breathing problems are well known to result in corresponding difficulties in sleep, including snoring, sleep apnea, restless sleep and corresponding daytime somnolence. These various problems are not only difficult for the subject, but for the sleeping partner of the subject as well. Reduced oxygenation due to breathing interruption during more severe episodes is particularly problematic, and extreme cases have been known to result in hypertension, cardiac arrhythmia, and even death due to breathing cessation during apnea.

The physical causes of the above problems are reasonably well understood, ranging from nasal turbinate hypertrophy to lingual and maxillary displacement to a narrowing of the pharynx due to partial obstruction by the soft palate and/or uvula. The latter syndrome is particularly likely when the soft palate and/or uvula are more flaccid than normal. Oral breathing to overcome this, particularly during sleep, tends to result in inferior and/or posterior displacement of the mandible and the base of the tongue, thereby exacerbating the problem.

Accordingly, a number of treatments have been developed over the years. Generally, less invasive treatments are attempted initially, e.g., continuous positive airway pressure (CPAP). However, when such treatment is ineffective, surgical treatment is often called for. Such surgical treatment may comprise one or more of a large number of different procedures, including septoplasty, turbinoplasty, tonsillectomy and/or adenoidectomy, uvulopalatopharyngoplasty, and/or possibly other procedures.

One such procedure comprises modification of the soft palate and/or uvula to stiffen these organs and to reduce their posterior displacement. This has been conventionally accomplished in the past by means of the placement of small implants in the soft palate, or by cauterizing or ablating the soft palate and/or uvula tissue to produce scarring of those tissues and to reduce their flaccidity. This may also result in some reduction in the size and/or posterior extension of these organs. These surgical procedures have been accomplished conventionally by accessing the inferior surface(s) of the soft palate and/or uvula through the mouth of the patient. The problem with accessing these structures orally is that the treatment is applied to the inferior surfaces of the organs, thus tending in many cases to draw the soft palate and/or uvula downward. This oral access technique may also result in some destruction of the oral mucosa, which is not desirable.

Thus, an endoscopic nasal palatoplasty procedure solving the aforementioned problems is desired.

SUMMARY OF THE INVENTION

The endoscopic nasal palatoplasty operation or procedure provides a surgical correction of the soft palate and/or uvula, resulting in some anterior displacement to at least the posterior portions of these organs due to tissue shrinkage after treatment. This opens up the nasopharyngeal region to promote nasal breathing and reduce oral breathing, thereby reducing snoring, sleep apnea, and other sleep-disordered breathing problems. However, rather than accessing the inferior surfaces of the soft palate and uvula through the mouth, the present endoscopic nasal palatoplasty procedure accesses the superior surface(s) of the soft palate and/or uvula by means of one of the nasal passages of the patient. The lesions formed by this surgery tend to draw the posterior portions of the soft palate and/or uvula forward, thereby increasing the size of the nasopharyngeal passage. The flaccidity of the soft palate and/or uvula are also reduced, thus increasing their resistance to oral airflow that might otherwise deflect them toward the nasal air passage to promote oral breathing.

Various surgical tools or implements may be used to perform the endoscopic nasal palatoplasty of the present invention, as desired. A preferred implement is a Coblator®("Coblator" is a registered trademark of ArthroCare Corporation of Austin, Tex.), a surgical instrument produced by Arthro-Care® ENT of Sunnyvale, Calif. The Coblator® is a dual-function implement. The extreme distal tip of the instrument produces a plasma that ablates the tissue into which the tip is inserted, thereby forming a channel in the tissue. Another element displaced from the extreme distal tip creates heat that results in coagulation of the ablative lesion to complete the treatment. Other surgical implements may be used in lieu of the Coblator®, e.g., an electro cauterizing implement, laser cauterizing implement, or other similar device. The endoscopic nasal palatoplasty procedure may be performed as a stand-alone procedure, or along with other related convention surgical procedures, such as septoplasty and/or turbinoplasty during the same operating session.

The penetration of the instrument tip substantially through the thickness of the soft palate and/or uvula results in the organs drawing or shrinking generally uniformly in an anterior direction, thereby increasing the space between the posterior surface of the uvula and the back of the nasopharyngeal passage to encourage nasal breathing and reduce oral breathing. This reduction in oral breathing produces a corresponding reduction in sleep-disordered breathing syndrome, thus providing relief for the patient and his or her sleep partner.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The endoscopic nasal palatoplasty is a surgical procedure adapted to treat the soft palate and/or uvula to promote their forward contracture, thereby further opening the space between the posterior portion of the uvula and the nasopharynx. The operation or procedure is adapted to treat the superior or upper surfaces of the soft palate and/or uvula, rather than the lower or inferior surfaces, as is conventionally done. The procedure may be performed under local anesthetic and/or on an outpatient or office treatment basis, depending upon the specific number of procedures to be performed and the judgment of the surgeon.

Figure 1:
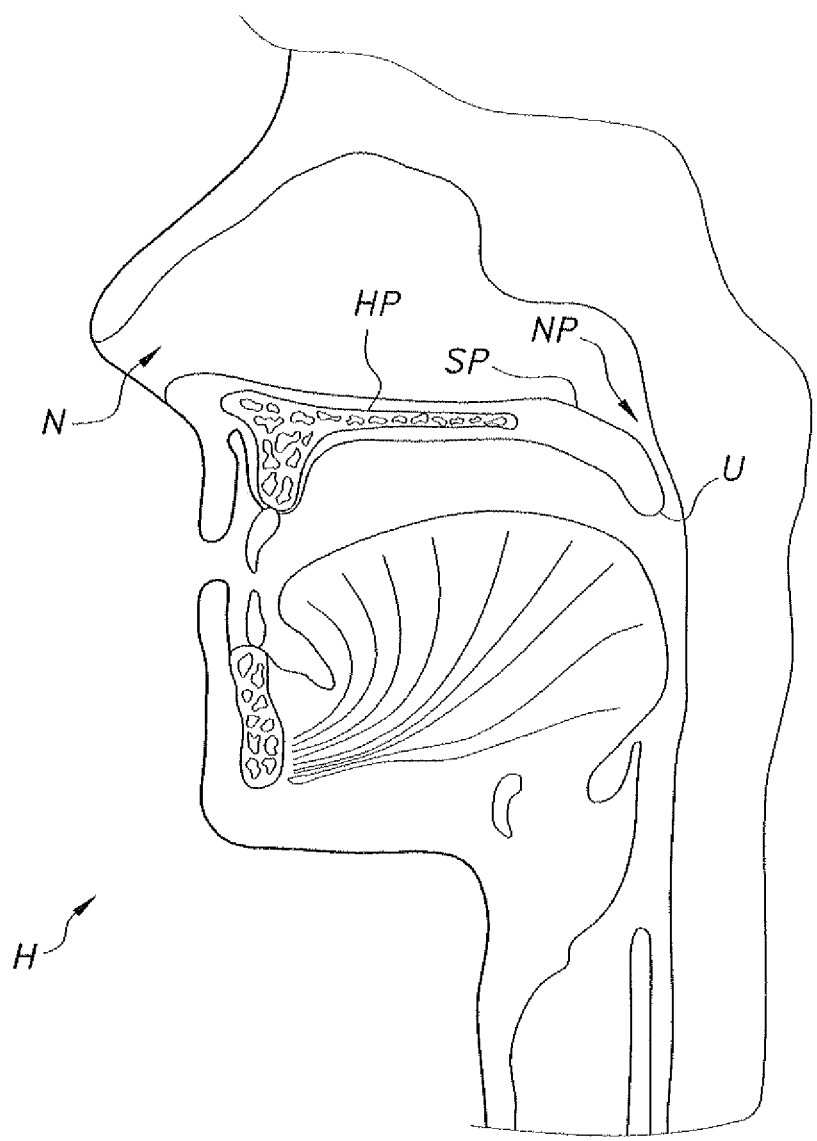
FIG. 1 is a prior art diagrammatic view of the anatomy of the lower portion of the human head, illustrating an exemplary restricted airway gap to be treated by the endoscopic nasal palatoplasty procedure according to the present invention.

FIG. 1 of the drawings is a prior art diagrammatic view of the anatomy of the lower and forward portion of an exemplary human head H having a reduced nasopharyngeal passage NP due to the posterior displacement of the soft palate SP and/or uvula U. The reduction in the area of the nasopharyngeal passage NP results in restricted airflow through the nose and corresponding greater airflow through the mouth, particularly during sleep. The oral airflow often results in vibration of the soft palate and/or uvula during sleep, i.e., snoring and other sleep related problems. Oral breathing may also result in various other problems, e.g., posterior displacement of the base of the tongue, inferior mandibular displacement, etc., all of which exacerbate sleep problems.

Figure 2:
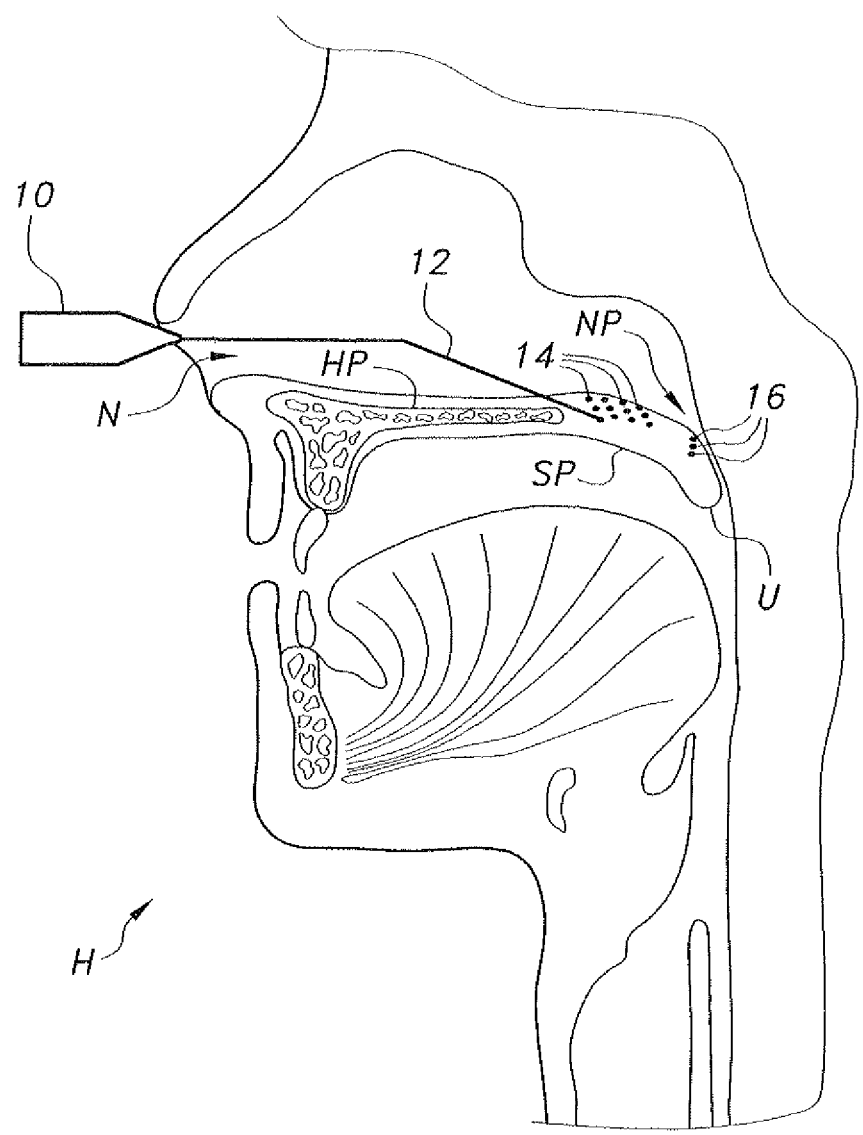
FIG. 2 is a diagrammatic view of the anatomy of the lower portion of the human head similar to FIG. 1, illustrating the placement of a surgical implement through one of the nasal passages to access the superior surface of the soft palate and/or uvula for performing the endoscopic nasal palatoplasty procedure of the present invention to relieve the obstruction of FIG. 1.
Figure 3:
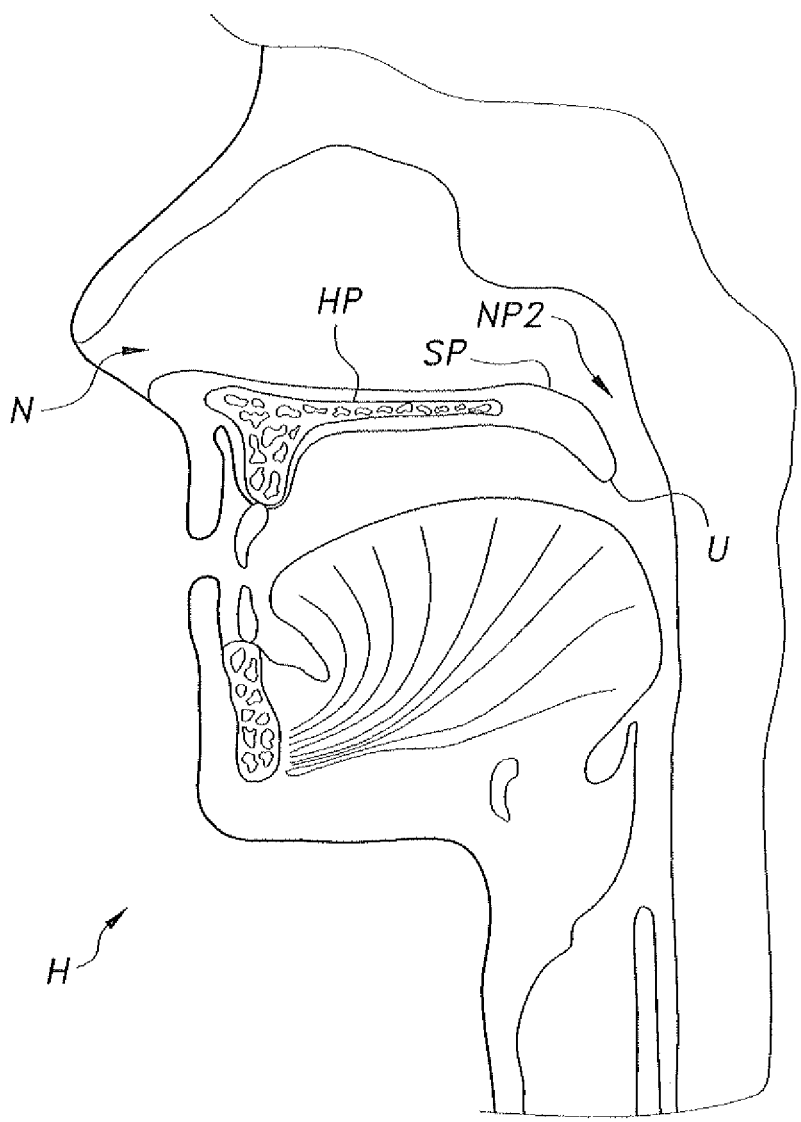
FIG. 3 is a diagrammatic view in section of the anatomy of the lower portion of the human head similar to FIGS. 1 and 2, illustrating the widened airway gap between the soft palate and uvula and the back of the throat after the endoscopic nasal palatoplasty procedure of the present invention.
Figure 4:
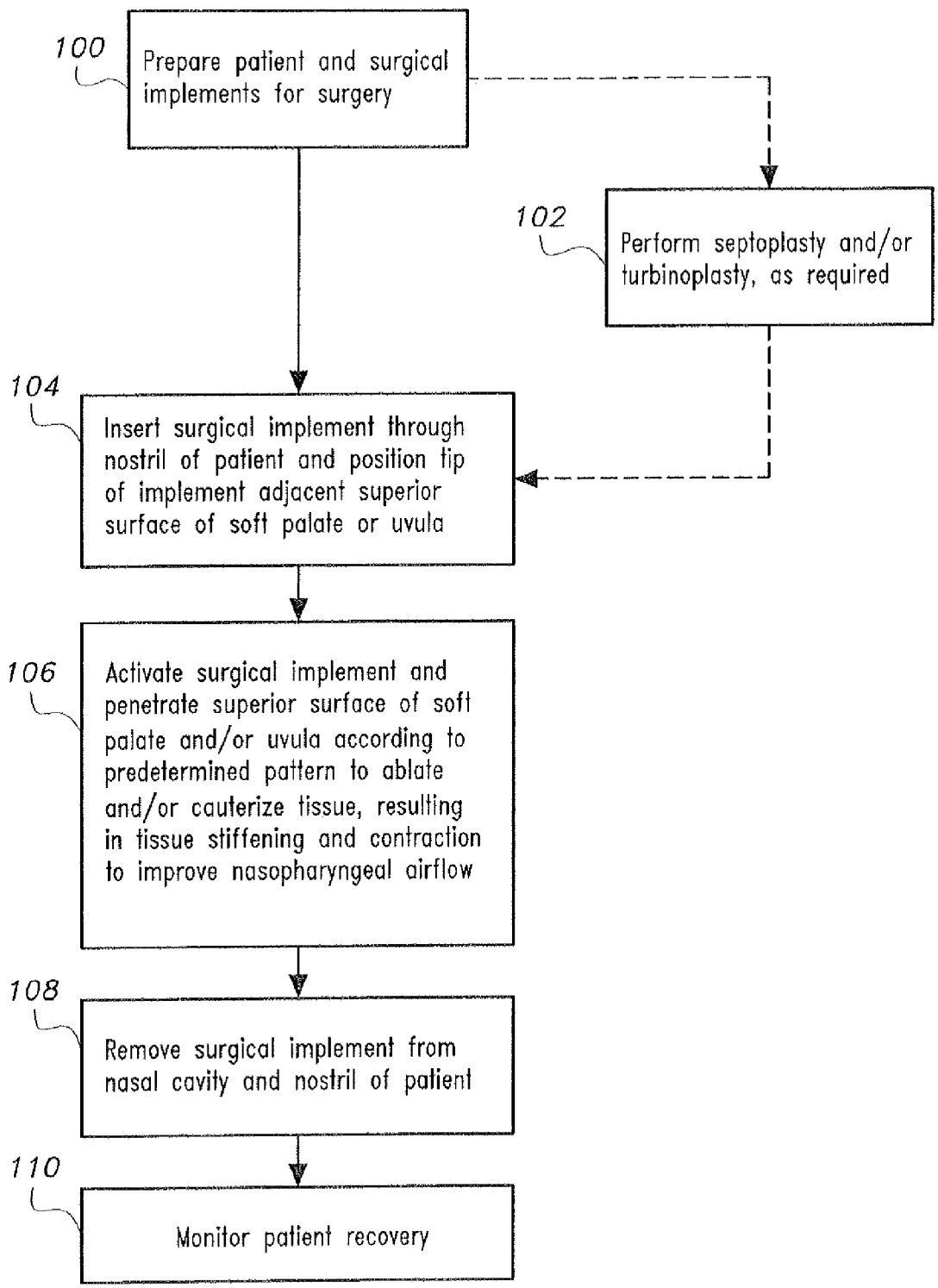
FIG. 4 is a flowchart briefly describing the steps of a method of performing an endoscopic nasal palatoplasty according to the present invention.

FIG. 2 of the drawings illustrates treatment of the soft palate SP by endoscopic nasal palatoplasty. FIG. 4 provides a flowchart briefly describing the steps in the method of carrying out the endoscopic nasal palatoplasty. The patient is initially prepared for the operation or surgical procedure in the conventional manner, generally as indicated in the first step 100 of FIG. 4. The specific steps involved in the preparation will depend upon the specific surgical procedures to be performed. For example, it may have been determined that the patient needs other surgery in addition to the endoscopic nasal palatoplasty procedure, such as septoplasty and/or some form of turbinoplastic procedure.

The appropriate surgical implements will be prepared for surgery, the specific surgical implements also depending upon the specific surgical procedure or procedures to be performed. In the case of the endoscopic nasal palatoplasty procedure, the preferred endoscopic surgical instrument or implement is the Coblator®, an electrical surgical implement manufactured by ArthroCare® ENT of Sunnyvale, Calif. The Coblator® is capable of producing a plasma field around the tip of the wand by generating radio frequency mediated through a fluid, such as saline, thereby ablating the surrounding tissue when inserted therein. Lower power may be provided to the device to produce coagulation of the lesion formed, if desired. Other conventional electrical and/or electronic surgical implements or instruments producing coagulation and/or cauterization may be used in lieu of the Coblator®, e.g., electro thermal and laser surgical implements.

When the patient and the instrument or instruments have been readied in accordance with the surgical procedure or procedures to be performed, the surgical procedure or procedures are performed. In many cases it may be necessary to perform some other surgical procedure or procedures prior to the endoscopic nasal palatoplasty procedure, e.g., septoplasty to correct the position of the nasal septum and/or turbinoplasty to correct some aspect of the nasal turbinates. These additional operations or procedures are indicated in the optional second step 102 of the flowchart of FIG. 4, as they will not be required in every instance.

At this point, the endoscopic nasal palatoplasty procedure is performed. As the name of the procedure indicates, the endoscopic implement 10 (e.g., Coblator®, etc.) is inserted through one of the nasal passages N of the patient and the distal tip of the wand 12 is positioned as desired. (Various other procedures are performed prior to insertion of the wand, e.g., treating the tip of the wand with a saline solution for better electro conductivity, but such procedures are conventional in the use of the device.) The drawing of FIG. 2 illustrates an exemplary procedure in which the distal tip of the wand 12 is repeatedly inserted into the superior surface of the soft palate SP to form a series of lesions 14. When a plasma-forming implement, such as the Coblator®, is used, each insertion and activation of the device results in the ablation of immediately adjacent tissue and formation of a small channel in the tissue at each penetration as a result of the plasma discharge within the tissue. Other electrical surgical implements may coagulate and/or cauterize the tissue, so that the end result is contracture of the treated tissue toward the area treated due to the necrosis and fibrosis resulting from the surgical treatment. This also results in reduction in the extent or size of the treated tissue or organ and a stiffening of the treated organ, thereby reducing the flaccidity of the tissue and enlarging the nasopharyngeal passage.

The distal tip of the wand 12 is inserted into the tissue for a depth on the order of one centimeter in accordance with the judgment of the surgeon, and the distal tip of the wand 12 is charged electrically for a period of about five to ten seconds, again in accordance with the judgment of the surgeon. The depth of penetration of the distal tip of the wand 12 and the duration of application are conventional steps in the method of using the Coblator® or other electrical surgical implement.

The treatment is repeated a plurality of times, in accordance with the judgment of the surgeon, as indicated by the completed lesions 14 formed in the superior surface of the soft palate SP, indicated by the small dots shown on that surface in FIG. 2. The penetrations of the superior surface of the soft palate SP are preferably carried out according to a predetermined plan or pattern. Preferably, a series of four to five such lesions are formed in a lateral row to each side of the soft palate SP, a total of eight to ten lesions per row, with multiple rows being formed and extending posteriorly from the juncture of the soft palate SP with the hard palate HP to the uvula U. (It will be noted that the surgical implement is removed and inserted through either nostril N according to the side of the soft palate SP upon which the treatment is being performed, during the duration of the procedure.) This part of the procedure is indicated generally by the fourth step 106 of the flowchart of FIG. 4.

In many instances, similar treatment of the superior surface of the uvula U may be indicated in lieu of or in addition to treatment of the superior surface of the soft palate SP described above. This may be accomplished in a similar manner to the procedure described above for treatment of the soft palate SP, i.e., preparation of the surgical implement as required, insertion of the wand of the implement through either nasal passage of the patient depending upon the lateral aspect of the uvula to be treated (both sides will typically be treated symmetrically, the surgical implement being removed and reinserted through the appropriate nasal passage), and penetration and electrical activation of the wand of the implement in accordance with the judgment of the surgeon. The result is the formation of a series of uvular lesions 16 on the superior surface of the uvula U, generally as indicated in FIG. 2 of the drawings. The resulting necrosis and fibrosis results in reduction in the extent or size of the treated tissue or organ and a stiffening of the uvula, thereby reducing the flaccidity of the tissue and enlarging the nasopharyngeal passage.

When the surgical procedure on the superior surface of the soft palate SP and/or uvula U has been completed, the surgical implement 10 with its wand 12 is withdrawn from the nasal passage NP of the patient and the patient is monitored during recovery, generally as indicated by the fifth and sixth steps 108 and 110 of the flowchart of FIG. 4. The various lesions 14 and/or 16 formed in the superior surfaces of the soft palate SP and/or uvula U in accordance with the procedure result in contraction and stiffening of the treated tissues or organs, as noted further above. The contracted soft palate and/or uvular tissues result in the enlargement of the nasopharyngeal passage, as indicated by the enlarged passage NP2 shown in FIG. 4, which represents the affected areas after treatment.

The increased area of the enlarged nasopharyngeal passage NP2, along with the reduction in flaccidity of the treated soft palate SP and/or uvula U, greatly enhance nasal aspiration and greatly reduce or eliminate vibration of the subject tissues, particularly during sleep, thereby providing greater comfort and freer breathing during sleep for the treated patient. Moreover, accessing the soft palate and/or uvula through the nasal passages obviates the need for an oral procedure where other nasal procedures (e.g., septoplasty and turbinoplasty) are also performed, thus leaving the oral passage intact during the healing of the nasal and/or superior surfaces of the soft palate and/or uvula and obviating disturbance or damage to the oral mucosa during the operating procedure.

It is to be understood that the present invention is not limited to the embodiments described above, but encompasses any and all embodiments within the scope of the following claims.

I claim:

1. A method of performing an endoscopic nasal palatoplasty procedure on a patient, comprising the steps of:
   (a) evaluating the patient to determine specific areas of operating procedures needed, wherein the specific areas of operating procedures needed are from the group consisting of a superior surface of a soft palate and a superior surface of a uvula;
   (b) selecting a specific area of the specific areas of operating procedures needed, based upon the evaluating;
   (c) providing at least one electric endoscopic surgical implement having a distal tip;
   (d) preparing the patient and the at least one electric endoscopic surgical implement for the endoscopic nasal palatoplasty procedure, wherein preparing the patient includes anesthetization;
   (e) inserting the at least one electric endoscopic surgical implement through a nasal passage of the patient;
   (f) penetrating the selected specific area of the patient at a predetermined location and to a predetermined depth using the distal tip of the at least one electric endoscopic surgical implement;
   (g) electrically actuating the at least one electric endoscopic surgical implement, thereby forming a lesion in the selected specific area of the patient;
   (h) repeating steps (f) and (g) a plurality of times forming a predetermined lesion pattern;
   (i) wherein the predetermined lesion pattern includes symmetric series lesions formed in lateral rows on each side of the selected specific area;
   (j) withdrawing the at least one electric endoscopic surgical implement from the nasal passage of the patient; and
   (k) monitoring a recovery of the patient.

2. The method of performing the endoscopic nasal palatoplasty procedure according to claim 1, wherein the selected specific area is the superior surface of the uvula.

3. The method of performing the endoscopic nasal palatoplasty procedure according to claim 1, further comprising the step of performing at least one operation selected from the group consisting of turbinectomies and septoplasties.

4. The method of performing the endoscopic nasal palatoplasty procedure according to claim 1, wherein the at least one electric endoscopic surgical implement generates a plasma the plasma ablating which ablates a portion of tissue of the selected specific area.

5. The method of performing the endoscopic nasal palatoplasty procedure according to the method of claim 1, wherein the at least one electric endoscopic surgical implement is an electrocautery needle.

6. The method of performing the endoscopic nasal palatoplasty procedure according to the method of claim 1, wherein the at least one electric endoscopic surgical implement is an electro thermal surgical implement for thermally cauterizing a portion of tissue of the selected specific area.

7. The method of performing the endoscopic nasal palatoplasty procedure according to the method of claim 1, wherein the at least one electric endoscopic surgical implement is a laser probe for thermally cauterizing a portion of tissue of the selected specific area.

8. The method of performing the endoscopic nasal palatoplasty procedure according to claim 1, wherein the selected specific area is the superior surface of the soft palate.

9. The method of performing the endoscopic nasal palatoplasty procedure according to claim 8, wherein the predetermined location is defined by a juncture of the superior surface of the soft palate with a superior surface of a hard palate, and extends posteriorly to the uvula.

10. The method of performing the endoscopic nasal palatoplasty procedure according to claim 1, wherein the selected specific area includes both the superior surface of the soft palate and the superior surface of the uvula.

* * * * *